United States Patent [19]
O'Dell et al.

[11] Patent Number: 5,385,821
[45] Date of Patent: Jan. 31, 1995

[54] METHOD FOR HYPOTHERMIC PRESERVATION OF LIVING TISSUE

[75] Inventors: Bobby J. O'Dell; Leonid Bunegin, both of San Antonio, Tex.

[73] Assignee: Board of Regents, The University of Texas System, Austin, Tex.

[21] Appl. No.: 276,938

[22] Filed: Jul. 19, 1994

Related U.S. Application Data

[62] Division of Ser. No. 29,688, Mar. 11, 1993, Pat. No. 5,362,622.

[51] Int. Cl.$^6$ .............................................. A01N 1/02
[52] U.S. Cl. ......................................... 435/1; 435/2; 604/19; 604/28
[58] Field of Search ...................... 435/1, 2, 283, 289; 604/19, 28, 30, 31, 34

[56] References Cited

U.S. PATENT DOCUMENTS

| | | |
|---|---|---|
| 3,777,507 | 12/1973 | Burton et al. |
| 3,814,934 | 6/1974 | Borsanyi |
| 3,843,455 | 10/1974 | Bier |
| 3,892,628 | 7/1975 | Thorne et al. |
| 3,914,954 | 10/1976 | Doerig |
| 3,935,065 | 1/1976 | Doerig ............................ 435/283 |
| 4,242,883 | 1/1981 | Toledo-Pereyra |
| 4,745,759 | 5/1988 | Bauer et al. |
| 4,837,390 | 6/1989 | Reneau |
| 4,951,482 | 8/1990 | Gilbert |

OTHER PUBLICATIONS

Petsika, et al., "Adenosine Enhances Left Ventricular Flow During 24-Hour Hypothermic Perfusion of Isolated Cardiac Allografts," 9 *J. Heart Transpl.* pp. 543–547 (1990).

Minten, et al., "Differerences in High-Energy Phosphate Catabolism Between the Rat and the Dog in a Heart Preservation Model," 10 *J. Heart and Lung Transpl.* pp. 71–78 (1991).

Wicomb, et al., "Value of Polyethylene Glycol (PEG) and Horseradish Peroxidases (HRD) for Hypothemeric Rabbit Heart Perfusion," 21 *Transpl. Proc.* pp. 1366–1368 (1989).

Qayumi, et al. , "Comparison of Functional and Metabolic Assessments in Perservation Techniques for Heart Transplantation,"4 *J. Investigative Surgery* pp. 93–102 (1991).

M. Yland, et al., "A Homeostatic Perfusion Method and Apparatus: A New Approach to In Vitro Hibernation," manuscript, Depts. of Surgery and Anesthesiology, University Hospital Stony Brook, Stony Brook, N.Y. (undated).

*Primary Examiner*—Jeffrey R. Snay
*Attorney, Agent, or Firm*—Arnold White & Durkee

[57] ABSTRACT

A method and apparatus is provided for long-term extracorporeal preservation of living tissue. A living tissue preservation device including a gas permeable membrane and perfusate allows oxygenation of the living tissue. The gas permeable membrane allows gas from a cyclically pumped source to permeate and expand the membrane, simultaneously oxygenating the perfusate and pumping the oxygen-enriched perfusate through the living tissue. Simply constructed of a few basic components into a single integrated container, the living tissue preservation device is capable of operating in many physical orientations, and requires no electrical power for operation. Also provided is a portable cold storage unit that is capable of receiving a living tissue preservation device and maintaining the tissue in the device at a substantially constant temperature of 4° C.±1° C. for at least 24 hours. Finally, a method of preserving extracorporeal living tissue incorporating the living tissue preservation device and cold storage unit is provided.

3 Claims, 5 Drawing Sheets

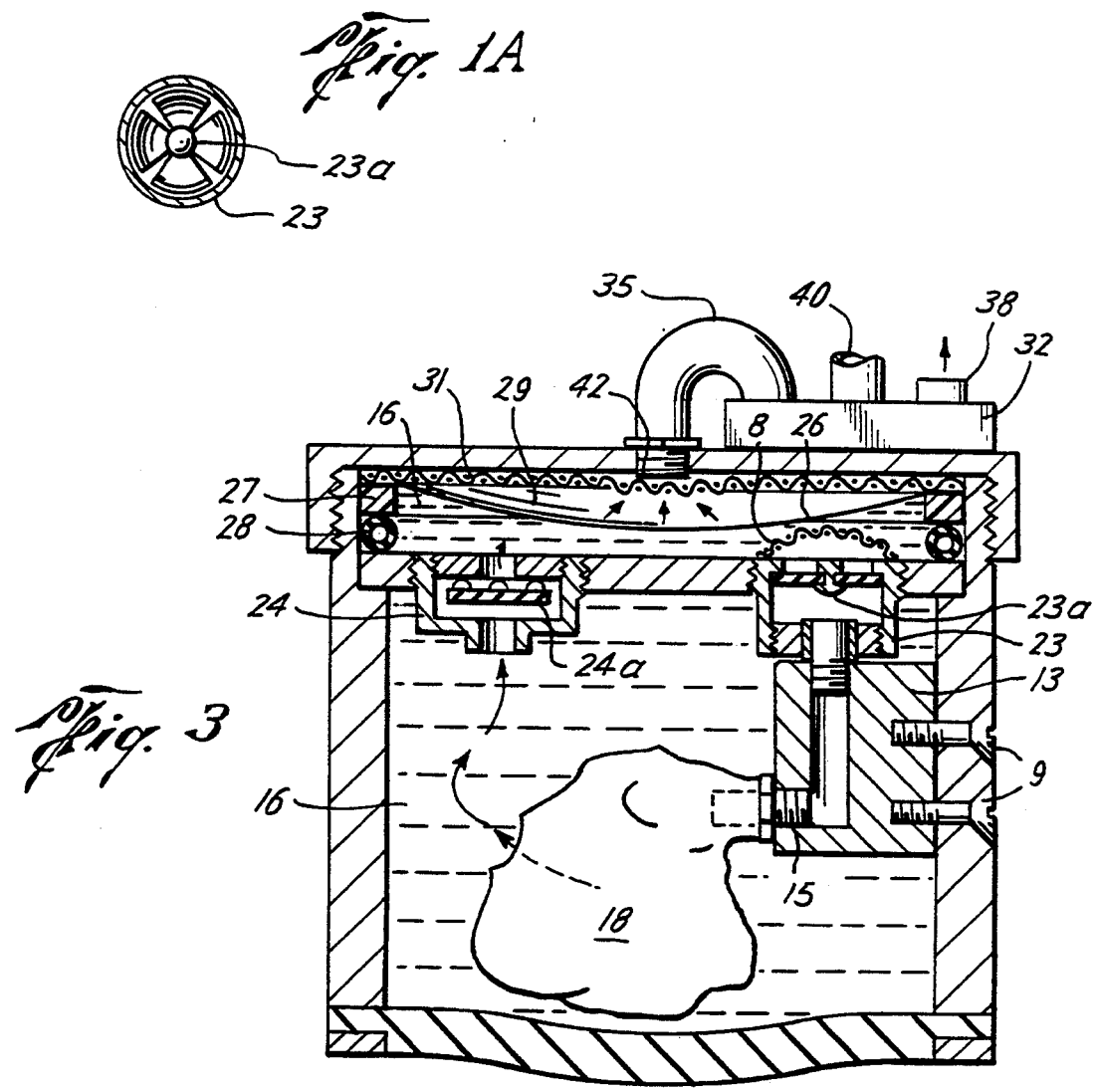
Fig. 1A
Fig. 3
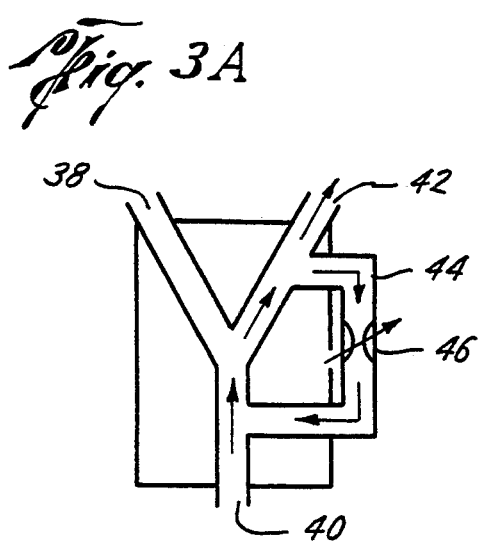
Fig. 3A
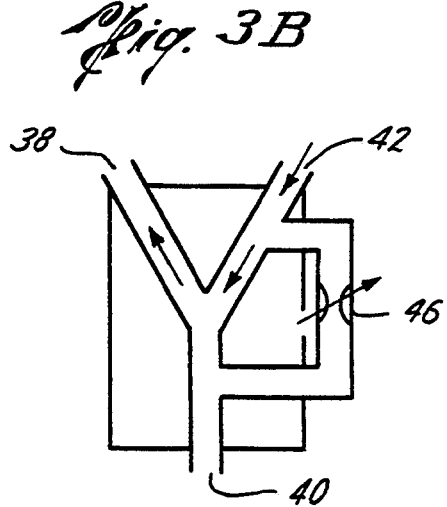
Fig. 3B

METHOD FOR HYPOTHERMIC PRESERVATION OF LIVING TISSUE

This is a division of copending application Ser. No. 08/029,688 filed Mar. 11, 1993, now U.S. Pat. No. 5,362,622.

BACKGROUND OF THE INVENTION

The present invention relates to a method and apparatus for highly portable, pulsatile perfusion for long-term extracorporeal preservation of the living tissue.

Although tissue transplantation and implantation have been viable since the 1960's, and have increased in popularity since that time, techniques for preservation of tissue have not become normalized. Initially, simple cold storage was used. Perfused cold storage and hyperbaric cold perfused storage were subsequently shown experimentally to be superior to simple unperfused cold storage. Since both techniques could not be practically applied, nonperfused cold storage continued to be preferred. A disadvantage of simple nonperfused cold storage, however, is the limited period of viability of the tissue, typically due to significant oxygen decline in the storage medium resulting from the stored tissue's metabolic need for oxygen.

Because of the distance that often separates tissue donors and recipients, the portability of storage devices is of critical importance. In addition, the desire to increase the pool of tissue available for transplantation into any one recipient mandates that the storage time for the tissue be extended beyond that permitted with simple hypothermic storage, thus opening the possibility for a world-wide network of donors and recipients.

Pulsatile perfusion devices have been developed to sustain and extend the viability of extracorporeal living tissue for several hours pending the implant of the tissue. The advantage of this technique is that it mimics the natural state of the tissue by inducing flow through its arterial supply with oxygenated fluid, or perfusate. However, only limited success has been achieved with perfusion of tissue in the atmosphere (i.e., without submersing the perfused tissue in the perfusate). The danger of this method of perfusion is that a pressure gradient may develop across the capillary wall of the tissue, which is proportionate to the output of the perfusion pump. Under hypothermic conditions, perfusion pressures in excess of 20 mm Hg have resulted in capillary damage destroying and compromising the viability of the tissue being preserved.

Hypothermic pulsatile perfusion of tissue during storage can significantly extend storage time to 12-24 hours, without loss of tissue viability, due to reduced tissue metabolic rate and oxygen consumption. For example, cooling to 15° C. reduces oxygen consumption of myocardial tissue to one-fifth of the rate at normal body temperature. However, hypothermia alone is less protective than when it is combined with oxygenated perfusion, in that a continuous supply of oxygen is available in the latter case to support the metabolic oxygen requirements.

Hypothermic perfusion devices have been designed and are known in the art. However, devices that are currently available for hypothermic pulsatile perfusion are large, require significant volumes of compressed gas and electrical power, and/or also may necessitate an upright level orientation for operation. Additionally, these devices are very complex, consisting of many intricate parts that must work precisely in concert.

One such device is that contemplated by Doerig, U.S. Pat. No. 3,914,954. Doerig appears to disclose an organ perfusion device that, in one embodiment, submerges the organ being preserved in the perfusate and pumps perfusate through the organ. The perfusate is oxygenated through a separate gas inlet valve. No provision is made, however, for sealing the perfusate from the lid of the device, thus leaving the perfusate open to the atmosphere, permitting the level of the perfusate to fluctuate, and providing a means by which biological or chemical contaminants can enter the system. Like most conventional perfusing units, the Doerig device is significantly limited in its portability due to the necessity of maintaining the device in an upright level orientation. Travel over extended distances, as is becoming increasingly necessary in modern times, would increase the likelihood of upsetting this delicate balance and endangering the organ. The additional requirement of large volumes of compressed oxygen and electrical power make usage of this apparatus impractical.

SUMMARY OF THE INVENTION

The problems outlined above are addressed by the apparatus and method of the present invention. That is, the invention makes it possible to produce a completely portable extracorporeal living tissue preservation device that is independent of electricity and is adjustable to operation in any physical orientation, yet includes pumping, oxygenating and chilling characteristics that can maintain the oxygenation and perfusion of living tissue for up to 24 hours or more.

Broadly speaking, the present invention contemplates a method and apparatus for hypothermic perfusion and oxygenation of extracorporeal living tissue. The apparatus includes a living tissue preservation device, which is comprised of a single chamber including a tissue compartment that is capable of receiving living tissue and perfusate. An interface plate having one-way inlet and outlet valves is secured in the chamber between the tissue compartment and a perfusing compartment, which also contains perfusate. A gas permeable membrane forms a pumping compartment by dividing the perfusing compartment from a top portion of the chamber.

A pumping device is coupled to the pumping compartment of the perfusion device, and is connectable to gas compression cylinders to cyclically force any properly proportioned oxygen-containing gas, such as 100% oxygen or a combination of oxygen and carbon dioxide, etc., into the pumping compartment. According to one aspect of the invention, gas is pumped into the pumping compartment by a fluidic logic device. Alternatively, gas may be pumped from a pressure controlled ventilator.

When the tissue is perfused, because the tissue is submerged in perfusate in a hermetically sealed container, each flow pulse results in a rise in pressure in both the capillaries as well as in the storage container. The result is that extremely small pressure gradients are generated across the capillary wall, potentially reducing damage and minimizing edema formation in the tissue being preserved.

An important feature of the present invention is the central role of the gas permeable membrane in the pumping compartment. The membrane performs multiple functions, including pumping perfusate from the perfusing compartment into the tissue compartment and allowing the exchange of gases in the perfusing compartment. Additionally, the membrane provides a seal between the perfusate and the pumping compartment, maintaining a constant level of perfusate. Because the perfusate is tightly sealed within the perfusing and tissue compartments, the device of the present invention is capable of operating during substantial physical reorientation. Thus, brief tipping of the container will not impair the operation of the device; however, adjustments to gas input pressure must be made to continue operation if the orientation of the device is significantly altered.

The present invention also contemplates a cold storage unit for chilling the living tissue and perfusate. This storage unit is preferably fabricated of a material having a high insulative index, such as styrofoam, and is subdivided into two chambers. A first chamber is capable of receiving the living tissue preservation device; a second chamber is capable of receiving a plurality of compressed oxygen cylinders. The oxygen cylinders may be connected in series to the tissue preservation device so that no disruption in oxygen flow is experienced upon the depletion of a cylinder. The first chamber is also capable of receiving a means for chilling the living tissue preservation device, preferably for at least 24 hours at a substantially constant temperature of $4°$ C.$\pm 1°$ C. The structure of this storage unit is described more fully in connection with a detailed description of the preferred embodiments.

The present invention also contemplates a method of perfusing extracorporeal living tissue, which includes attaching the arterial supply (if any) of the living tissue to a tube adapter and placing the connected tissue into the perfusate-filled tissue compartment of the device. The tube adapter is then connected to the inlet valve to allow perfusate flow from the perfusing compartment into the tissue. Oxygenation of the perfusate and tissue is then accomplished by supplying compressed, properly proportioned, oxygen-containing gas to the pumping compartment, injecting the gas at regular intervals into the pumping compartment, and pressurizing the gas side of the membrane. Gas permeates the membrane and oxygenates the perfusate in the perfusing compartment. Simultaneously, expansion of the membrane between the pumping compartment and the perfusing compartment pumps the oxygenated perfusate into the tissue through the one-way inlet valve. During the perfusing cycle, pressure builds up in the tissue compartment. This pressure is equalized by the membrane and the weight of the perfusate reserve. After the pressure cycle, the one-way outlet valve opens, allowing the level of fluid to equalize between the two compartments. This action causes fluid from the tissue compartment to flow through the outlet valve to the perfusing compartment where the dissolved gas, now comprising carbon dioxide, is permeated through the membrane and removed from the pumping compartment by the pumping device. The cycle is repeated at the next gas injection interval.

As noted earlier, hypothermia of the tissue and perfusate may extend the viability of the tissue. A preferred storage temperature is $4°$ C.$\pm 1°$ C., which may be attained by placing the device into the cold storage unit of the present invention packed with ice packs.

The present invention therefore provides an improved apparatus and method that allow convenient and relatively long-term storage and transportation of living tissue. The single chamber design renders the tissue preservation device relatively compact, and the existence of only a few primary parts renders it relatively simple in design and inexpensive to manufacture. Further, the size and structure of this device facilitate inducement of hypothermia through placement of the device in the compact, portable cold-storage unit of the present invention, thus extending the viability of the living tissue during storage or transportation. Portability of living tissue is enhanced by the perfusion device's electricity-free operation and adjustability to physical orientation.

The ability of the present invention to extend the preservation of living tissue has the following benefits:

1. The geographical area from which tissue could be obtained would be increased, thereby increasing tissue availability;
2. The increased tissue availability would increase the quality of tissue cross-matching, thus reducing rejection;
3. With longer tissue viability periods, tissue transplantation may potentially be moved from a high priority emergency procedure to possibly a scheduled procedure; and
4. Since donor tissue would be in better condition after storage according to the present invention, transplantation success rates should improve.

The advantages of the present invention will be further appreciated from the drawings and from the detailed description provided below.

BRIEF DESCRIPTION OF THE DRAWINGS

The herein described advantages and features of the present invention, as well as others which will become apparent, are attained and can be understood in more detail by reference to the following description and appended drawings, which form a part of this specification.

It is to be noted, however, that the appended drawings illustrate only exemplary embodiments of the invention and are therefore not to be considered limiting of its scope, for the invention may admit to other equally effective embodiments.

FIG. 1A is a cross-section view of the inlet valve of the apparatus of FIG. 1 through section 1A—1A.

FIG. 3 is a cross-section view of a perfusion apparatus according to the present invention during a gas exhaust cycle.

FIG. 3A is a diagram of gas circulating within a fluidic logic pumping device used during the gas input cycle according to the present invention.

FIG. 3B is a diagram of gas circulating within a fluidic logic pumping device used during the gas exhaust cycle according to the present invention.

DETAILED DESCRIPTION OF THE PREFERRED EMBODIMENTS

Figure 1:
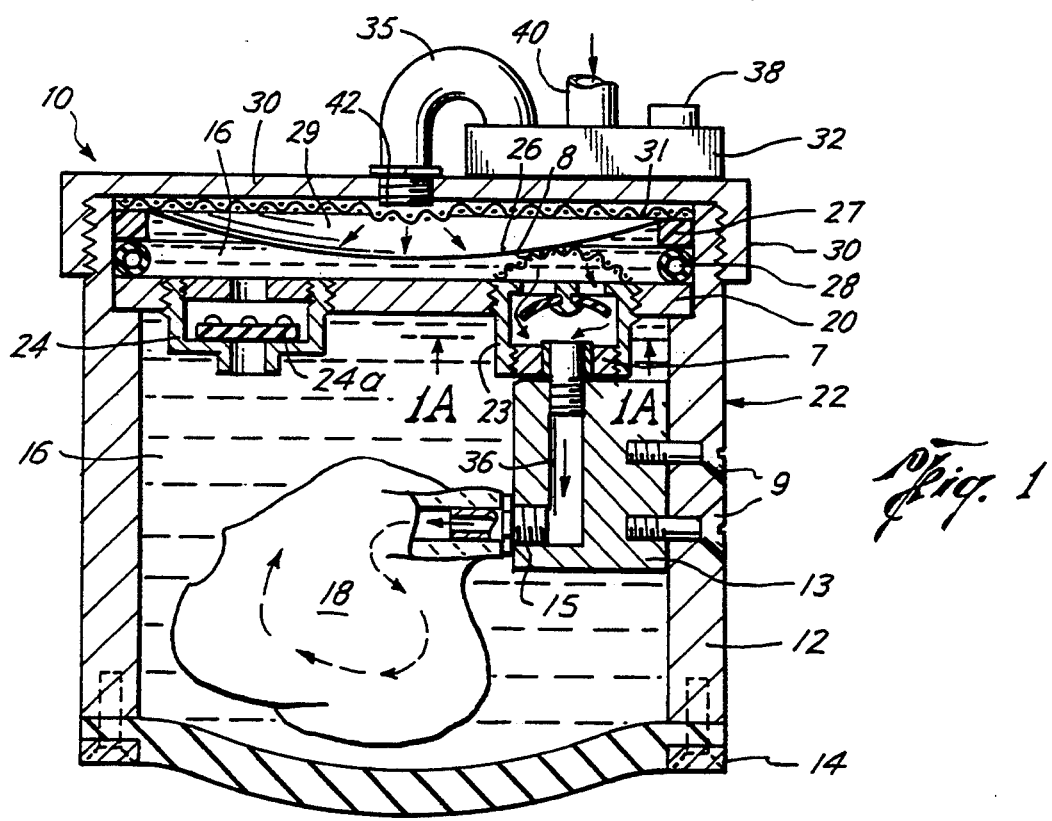
FIG. 1 is a cross-section view of a perfusion apparatus according to the present invention during a gas input cycle.

Turning now to the drawings, FIG. 1 is a cross-section view of an embodiment of the present invention for preserving extracorporeal living tissue. The apparatus comprises a chamber 10 that is capable of receiving living tissue 18 and perfusate 16. Chamber 10 as illustrated has rigid side walls 12, and a flexible compliant bottom 14. Alternatively, chamber 10 itself may be constructed entirely of flexibly compliant material, such as rubber or plastic. The function of one or more flexible walls is to accommodate increases in fluid pressure during the pumping cycle. Interface plate 20 is positioned within chamber 10 separating tissue compartment 22 from perfusing compartment 25. Interface plate 20 includes one-way inlet valve 23, which is capable of receiving oxygenated perfusate 16 from perfusing compartment 25 and directing its flow into inlet tube 36 and into living tissue 18 during the gas input cycle. When interface plate 20 is in place, one end of inlet tube 36 fits within grommet 7 for stability. For added stability, inlet tube 36 is preferably affixed to one wall of tissue compartment 22 by organ holding bracket 13. Screws 9 are shown affixing bracket 13 to wall 12. Other methods of sturdy, sanitary affixation are also suitable. Interface plate 20 also includes one-way outlet valve 24, shown sealed in FIG. 1. Gas permeable membrane 26 divides perfusing compartment 25 from a cavity within the chamber 10, forming pumping compartment 29. Chamber 10 is sealed with lid 30, to which a pumping device, illustrated in FIG. 1 as fluidic logic pumping device 32, is coupled to force a properly proportioned, oxygen-containing gas from one or more compressed gas cylinders (see FIGS. 9 and 10) through gas inlet port 42 and into pumping compartment 29, as shown in FIG. 1.

During oxygenation, shown in FIG. 1, fluidic logic pumping device 32 pumps gas into pumping compartment 29. The increased oxygen concentration in pumping compartment 29 causes gas to permeate membrane 26 and oxygenate perfusate 16 in perfusing compartment 25. Simultaneously, the difference in pressure expands membrane 26, which forces oxygenated perfusate from perfusing compartment 25 into inlet valve 23 and through inlet tube 36 into living tissue 18. Screen 8 may be provided to prevent the membrane from being pushed against valve 23. Flexible compliant bottom 14 of chamber 10 expands, as shown in FIG. 1, to accommodate the increased compartment volume caused by introduction of oxygenated perfusate 16 into living tissue be and tissue compartment 22.

When assembled, chamber 10 forms a hermetically sealed unit, which may be operated in any physical orientation with appropriate adjustments to the gas pressure injected into pumping compartment 29. Perfusate 16 is maintained at a constant level in chamber 10 by gas permeable membrane 26, which is sealingly positioned over perfusate 16 in perfusing compartment 25 by the tight fit of circular flexible tube, or "o-ring" 28 (such as a Silastic TM brand tube, manufactured by Dow Corning), membrane support 27, and chamber lid 30. A screen 31 may be positioned to create a small cavity under lid 30 to ensure that the reverse pressure during the gas outlet cycle does not trap membrane 26 against lid port opening 42 for gas inlet tube 35.

An exemplary gas permeable membrane 26 contemplated by the present invention has the following properties:

Oxygen permeability at 4° C.: 3,500 ml $O_2$/min/m$^2$
$CO_2$ permeability at 4° C.: 21,000 ml $CO_2$/min/m$^2$
Membrane thickness: 0.09 mm maximum
Porosity: Membrane porosity should be sufficient to prevent diffusion of water in its liquid phase.
Elasticity: Minimum elongation at break 30%; minimum burst strength 10 psi.

Suitable materials include silicone rubber, polydimethylsiloxane (PDMS), polytetrafluorethylene (PTFE), dimethyl and methyvinyl siloxane copolymers both unsupported and supported on polyester, or like fibers. Commercially available membranes meeting these specifications include the True Membrane TM manufactured by Avcore, Inc. of Plymouth, Minn., the Silon TM membrane manufactured by Bio Med Sciences, Inc. of Pennsylvania, and the Silastic TM membrane, manufactured by Dow Corning of Midland, Mich.

Preferred perfusate 16 is the University of Wisconsin Solution with HES or PEG, as referenced in Wicomb et al., 48 Transplantation 6–9 (1989) and 49 Transplantation 261–64 (1990), the disclosures of which are expressly incorporated herein by reference. Other general categories of acceptable perfusion/storage media compatible with the present invention include the perfusion/storage media described in the following references, disclosures of which are each expressly incorporated herein by reference:

1. Modified Krebs-Henseleit Solution, as referenced in Petsikas et al., 9 J. Heart Transplantation 543–547 (1990).
2. Bretschneider HTK Solution, as referenced in Minten et al., 10 J. Heart and Lung Transplantation 71–78 (1991).
3. Wicomb Solution, as referenced in Wicomb et al., 21 Transplantation Proceedings 1366–68 (1989).
4. Tyers' Solution, as referenced in Qayumi et al., 4 J. Investigative Surgery 93–102 (1991).

FIG. 1A shows flexible rubber diaphragm 23a of inlet valve 23. The leaf design of diaphragm 23a allows oxygenated perfusate to flow one way only from perfusing compartment 25 to tissue compartment 22. Additionally, any of a number of designs that allow for minimal restriction to perfusate flow will suffice for inlet valve 23.

Figure 2:
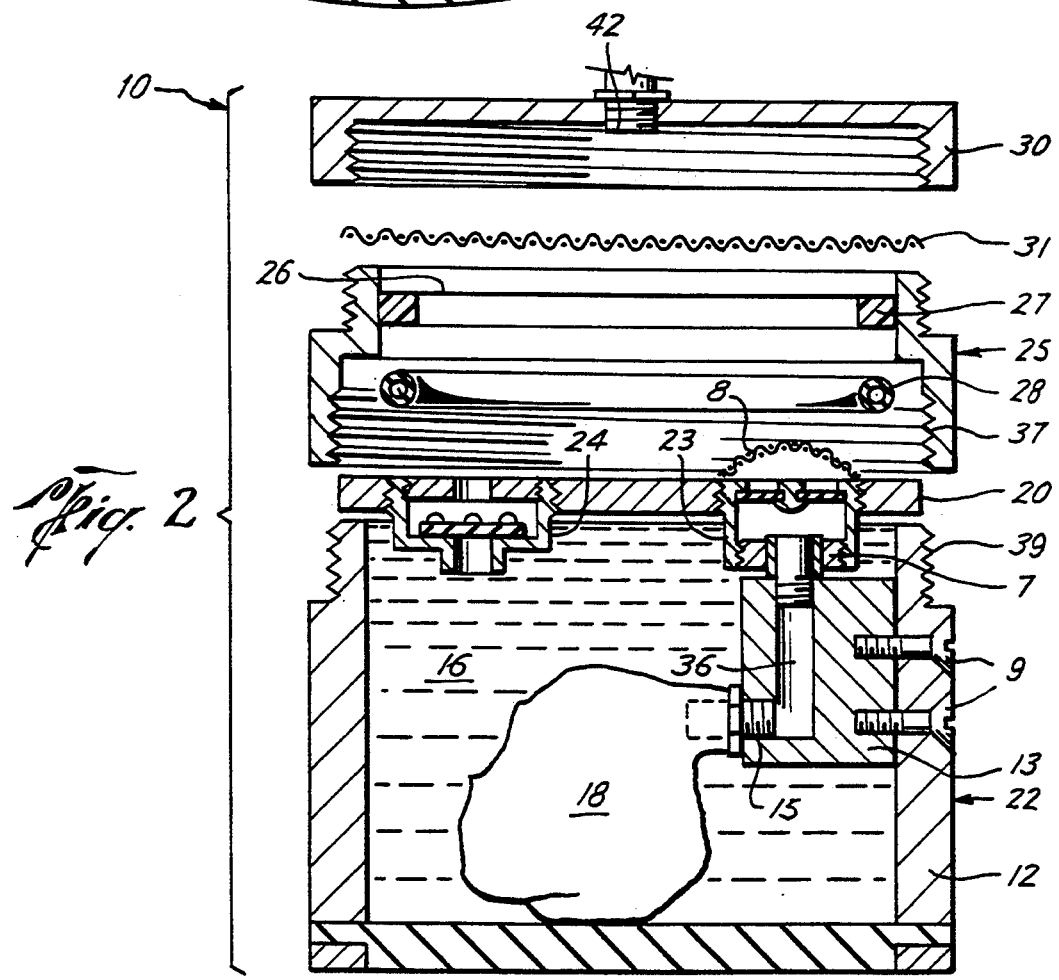
FIG. 2 is an exploded view of a perfusion apparatus according to the present invention.

As can be readily seen from the embodiment depicted in FIG. 2, chamber 10 may be simply constructed of only a few basic components. The primary portion of chamber 10 is tissue compartment 22. In the preferred method according to the present invention, perfusate 16 is introduced into tissue compartment 22, and the arterial supply (if any) of living tissue be is attached to tube adapter 15. Tissue be and tube adapter 15 are submerged into perfusate 16 within tissue compartment 22, and tube adapter 15 is then connected to inlet tube 36, which is preferably secured to a wall of tissue compartment 22 by, for example, tissue holding bracket 13, to stabilize the position of tissue 18. After tissue 18 is placed into perfusate 16, tissue compartment 22 is sealed by interface plate 20, and inlet tube 36 is in turn attached to inlet valve 23 of the interface plate 20. Additional perfusate 16 is then added to perfusing compartment 25.

Within perfusing compartment 25, an o-ring constructed of flexible tubing 28 (such as Silastic ™ brand tubing) is placed directly on top of interface plate 20, to produce a snug fit when membrane 26, bounded by membrane support 27, and lid 30 are stacked and sealed, completing integration of chamber bO. Although lid 30 is shown threaded for attachment to perfusing compartment 25, other methods of creating a tight, sealed fit are acceptable, such as latches, straps, clamps, snap caps, or other methods that meet the essential criterion of providing a snug, hermetically sealed connection between the individual compartments. Once lid 30 is attached, pumping compartment 29 is formed in the cavity between lid 30 and membrane 26. To prevent membrane 26 from being trapped against the lid opening 42 for gas inlet tube 35, screen 31 may be placed within pumping compartment 29 between membrane 26 and lid 30.

FIG. 2 illustrates a stacked compartment design in accordance with the present invention. Attached to tissue compartment 22 is perfusing compartment 25. As shown in FIG. 2, perfusing compartment 25 contains threads 37 in the interior of the lower portion of its walls, which are designed to interlock snugly with matching threads 39 on the exterior of the upper portion of the walls of tissue compartment 22. Other methods of creating a tight, sealed fit are acceptable, as noted above.

The stacked compartment design illustrated in FIG. 2 is not considered to be an essential feature of the present invention, but is one embodiment because it is quickly and easily constructed. Alternatively, as illustrated in FIG. 1, the unit may be comprised of a single container, with means, such as a holding bracket or ridge 21, for securing interface plate 20 within the container to separate tissue compartment 22 from perfusing compartment 25.

FIG. 3 illustrates the living tissue preservation device of FIG. 1 during the gas exhaust cycle. When the entry of the gas into pumping compartment 29 ceases, the pressure is relieved, relaxing membrane 26. This drop in pressure in turn closes one-way flexible diaphragm 23a of inlet valve 23, and raises stiff rubber disk 24a, thus opening one-way outlet valve 24 to allow gas-enriched perfusate to flow from tissue compartment 22 into perfusing compartment 25. Pressure during pumping holds disc 24a so that outlet valve 24 is closed. During the exhaust cycle, pressure is released, and disc 24a is pushed up by the exhaust pressure in tissue compartment 22, opening outlet valve 24. In the perfusing compartment 25, gas from the perfusate 16, which now has a concentration of carbon dioxide expelled from tissue 18, permeates membrane 26 into pumping compartment 29, where it is expelled through lid port 42 and in turn through gas exhaust port 38.

FIG. 3A illustrates the operation of fluidic logic device 32 during the gas input cycle. Properly proportioned gas from compressed gas cylinders (see FIGS. 9 and 10) enters gas inlet port 40, and flows as shown into lid port 42 to pressurize pumping compartment 29. Feedback circuit 44 of fluidic logic device 32 simultaneously experiences flow. When the flow in feedback circuit 44 exceeds the flow to pumping compartment 29, supply flow switches back to gas exhaust port 38, as shown in FIG. 3B. When the volume of gas from the previous pressurization cycle is vented, exhaust flow to gas exhaust port 38 falls to zero, and the supply flow then switches to provide flow to gas inlet port 40, repeating the cycle.

Regulator 46 in feedback circuit 44 controls the pulse duration and rate. At the preferred maximum allowable pumping pressure (50 mm Hg), output flow should not exceed 0.03 cubic feet per minute; thus, over a 24-hour period, a maximum expected gas usage should not exceed 40 cubic feet, independent of tissue weight. A suitable fluidic logic device 32 is an OR/NOR monostable amplifier, which operates on the Coanda principle and is available through Teknocraft, Inc., Palm Bay, Fla.

Figure 4:
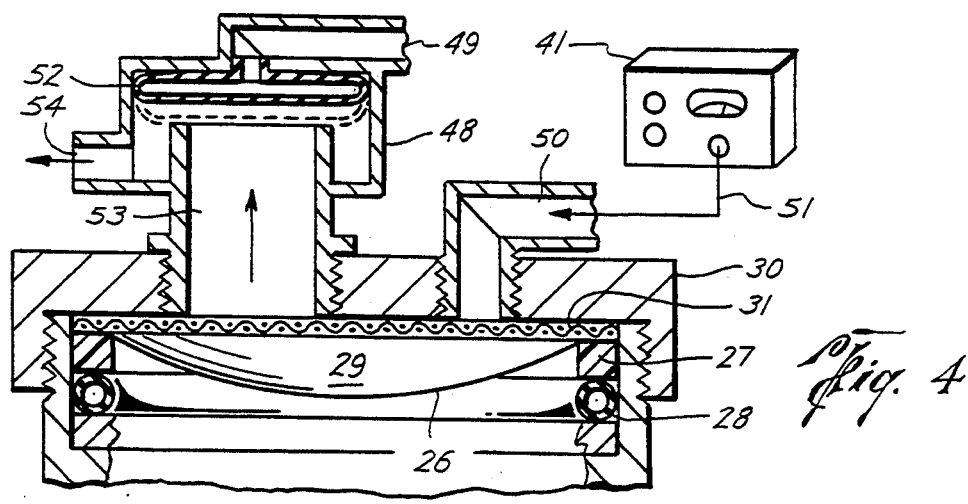
FIG. 4 is a cross-section view of a gas inlet/outlet device that may be used in accordance with the present invention.

FIG. 4 illustrates an alternative gas inlet/outlet device. This device comprises gas inlet valve 50 and exhaust valve 48. Properly proportioned, oxygen-containing gas is pumped from pressure controlled ventilator 41, such as a Mark 7 or Mark 14 model manufactured by Bird Corporation, or a Healthdyne Impulse Ventilator Model 303, through connective tubing 51 into gas inlet valve 50 and through gas inlet port 49 into gas exhaust valve 48. During gas input, bladder 52 in the exhaust valve expands to seal exhaust channel 53. Simultaneously, gas pumped into inlet valve 50 enters pumping compartment 29. During the off cycle of pressure controlled ventilator 41, bladder 52 in exhaust valve 48 is relaxed, as shown in FIG. 4, allowing gas to be exchanged in the pumping compartment 29, and released through exhaust channel 53 and out gas exhaust port 54. A gas exhaust valve 48 that performs as described above is an expiratory valve manufactured by Bird Corporation, model number 999-2576.

Figure 9:
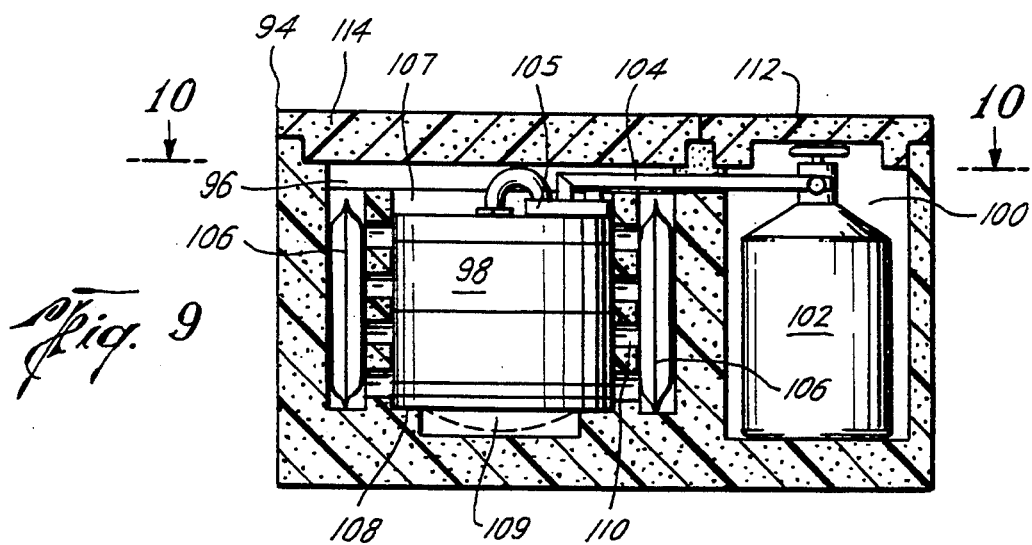
FIG. 9 is a section through a cold storage unit in accordance with the present invention for the container 10 apparatus shown in FIG. 1.

FIG. 9 shows a section through cold storage unit 94, which is constructed of a material having a high insulative index, such as styrofoam. The unit is divided into two primary chambers, first chamber 96 and second chamber 100. Access to the two chambers is preferably via two separate lids, 114 and 112, respectively. Second chamber 100 is constructed to hold a plurality of compressed gas cylinders 102, each containing a properly-proportioned, oxygen-containing gas. First chamber 96 is designed to receive tissue preservation device 98, which fits snugly within pocket 108. Additionally, depression 109 may be located within pocket 108 to permit expansion of the base of tissue preservation device 98 during oxygenation cycles. Pocket 108 is centrally located within a substantially cylindrical cavity 107 created by insulative, perforated barrier 110. These perforations permit movement of the heat from tissue preservation device 98 to cold packs 106, which line the inner perimeter of first chamber 96, exterior to insulative barrier 110.

Figure 10:
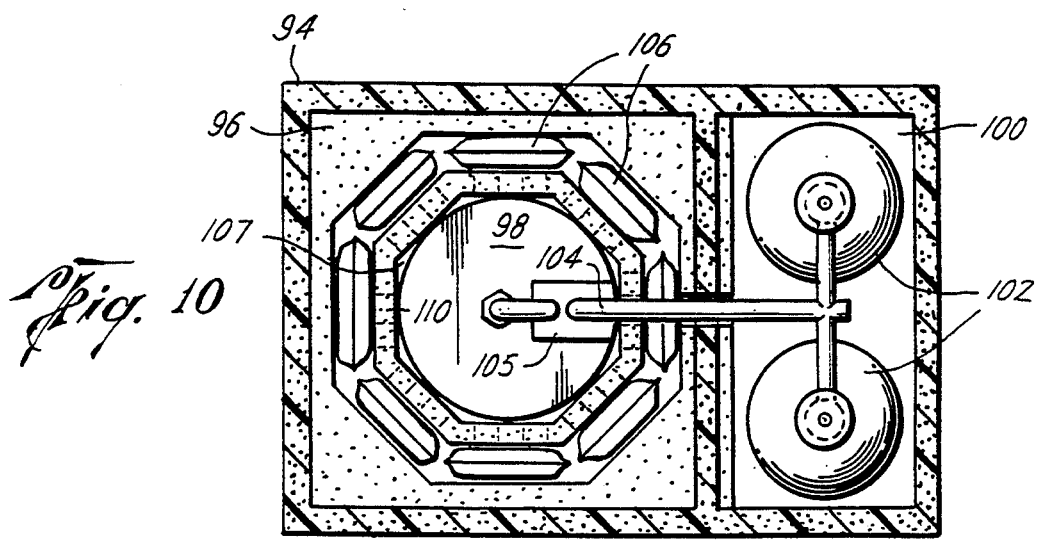
FIG. 10 is a section through section 10—10 of the cold storage unit depicted in FIG. 9.

FIG. 10 illustrates a top view of cold storage unit 94 along plane 10-10 of FIG. 9. FIG. 10 more clearly illustrates first chamber 96, which comprises perforated barrier 110 surrounding tissue preservation device 98, which is snugly placed within pocket 108 in cavity 107. Pocket 108 is designed to exactly admit the base of tissue preservation device 98 so as to hold it tightly and restrict independent movement thereof. The dimensions of cavity 107 created by perforated barrier 110 are such that positioning of tissue preservation device 98 permits a clearance between the preservation devices's outer wall and the inner wall of perforated barrier 110. This clearance is important in that it helps prevent freezing of the perfusion solution located within tissue preservation device 98. As shown in FIG. 10, compressed gas cylinders 102 are connected to fluidic logic device 105 via channel 104.

Lining the perimeter of perforated barrier 110 are a plurality of cold packs 106. These cold packs 106 preferably have a heat capacity capable of absorbing heat from tissue preservation device 98 and its contents (i.e., living tissue and perfusate), as well as maintaining a constant temperature of 4° C.±1° C. for 24 hours. Suitable cold packs include X-Coldbrick ™ cold packs, manufactured under model number XC24BR by Pelton Shepherd Industries of California. Approximately two cold packs per 500 cc's of perfusate solution can maintain the tissue and solution at 4° C.±1° C. for as long as 24 hours.

Figure 5:
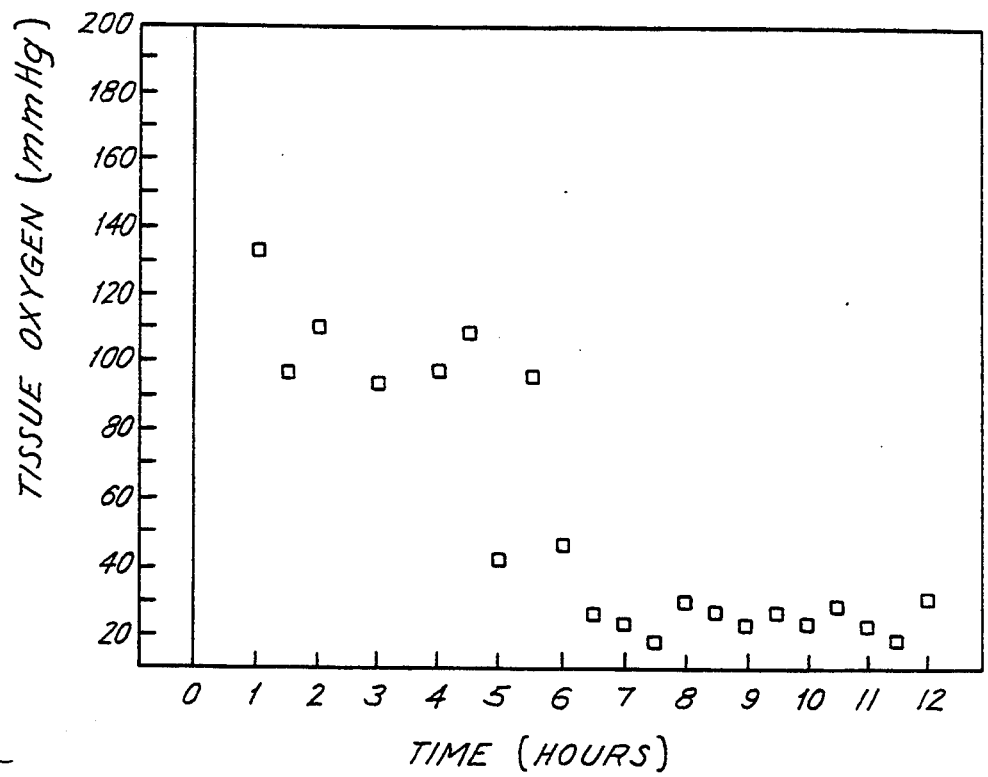
FIG. 5 is a graph illustrating the partial pressure of oxygen over several hours in tissue preserved by simple hypothermic storage.

Clinical trials of prototypes of the claimed tissue preservation apparatus and cold storage unit on canine hearts have successfully perfused and chilled the organs for at least 12 hours, as opposed to the 4 to 5 hours permitted with simple hypothermic storage. FIG. 5 illustrates actual results of the rapid decline in the partial pressure of oxygen in the tissue after 5 hours in simple hypothermic storage (such as storage of the tissue in a container packed in ice).

Figure 6:
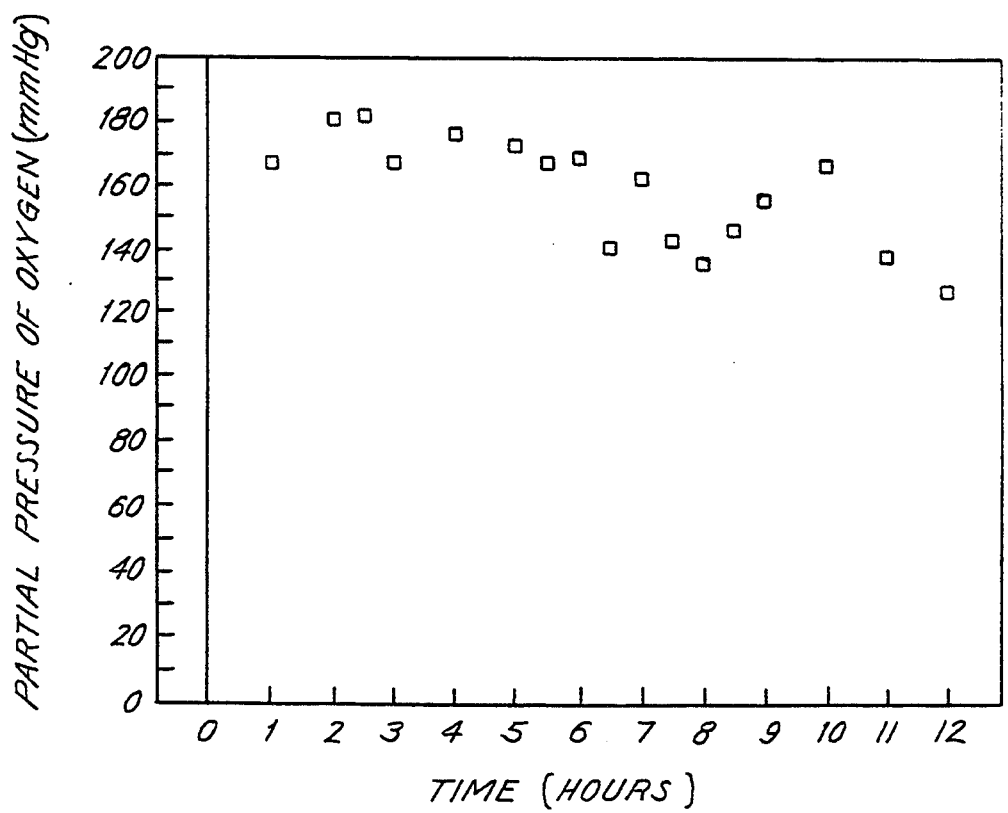
FIG. 6 is a graph illustrating the partial pressure of oxygen over several hours in tissue hypothermically perfused according to the present invention.

In contrast, FIG. 6 illustrates actual results of satisfactory levels of oxygen (i.e., $O_2$ partial pressure above 120 mm Hg) for at least 12 hours in tissue hypothermically perfused in accordance with the present invention.

Figure 7:
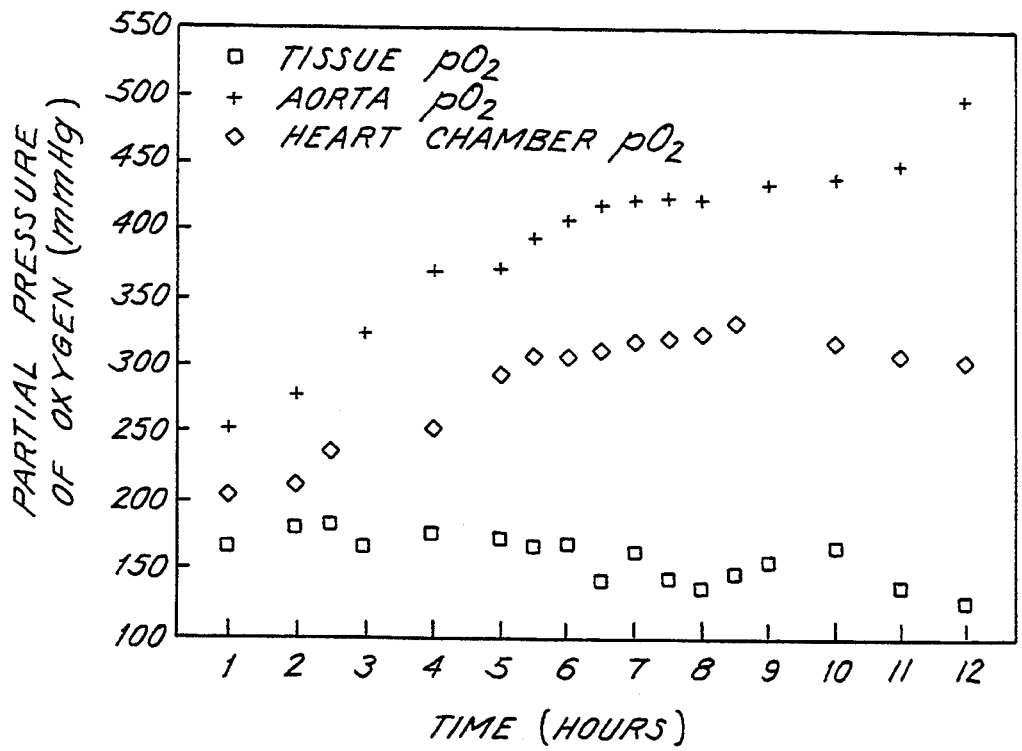
FIG. 7 is a graph illustrating the relative levels of oxygen in the cardiac tissue, in the artery of the tissue, and also in the tissue compartment, the results of which were compiled during a test of a perfusion device according to the present invention.

The relative levels of oxygen in the cardiac tissue, as taken from the tissue muscle, from the artery of the tissue, and also from the tissue compartment are illustrated in FIG. 7, the results of which were compiled during tests of a device constructed in accordance with the present invention.

Figure 8:
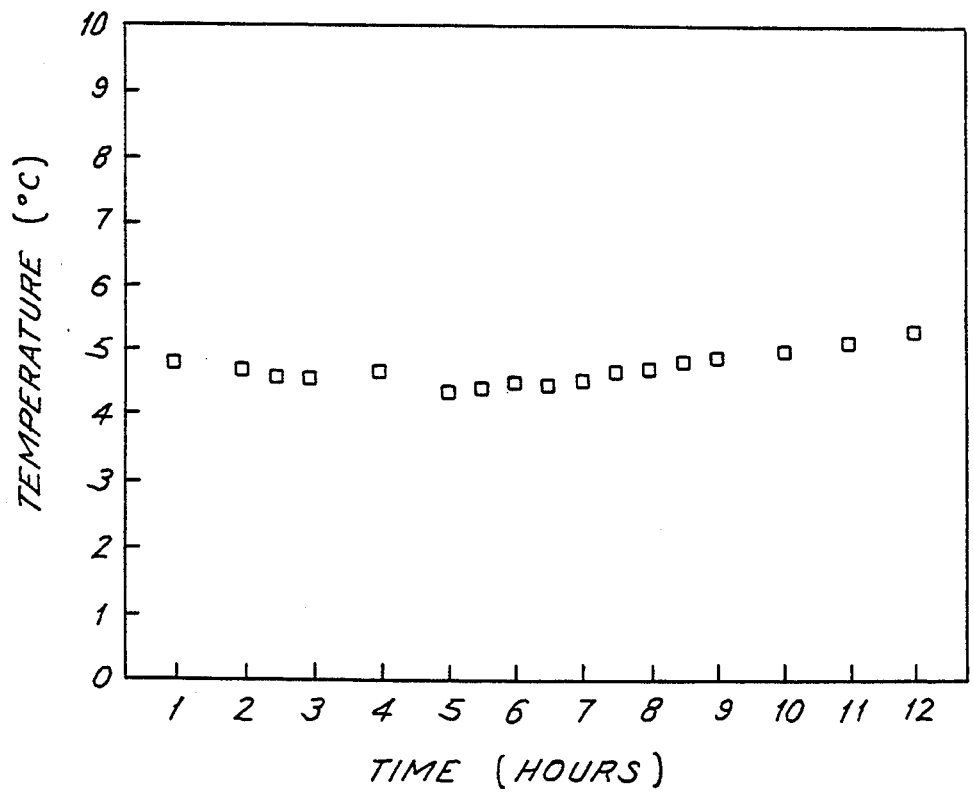
FIG. 8 is a graph illustrating temperature over time in tissue in perfusion apparatus chilled according to the present invention.

Lastly, FIG. 8 illustrates the relatively constant hypothermic temperature that can be maintained for at least twelve hours in accordance with the present invention, using, for example, X-Coldbrick ™ ice packs.

The present invention is not limited to preserving myocardia; any living tissue in which the main arterial supply vessel can be isolated and cannulated can potentially be stored in the claimed device. This includes organs such as lungs, kidneys, livers, and pancreas, and extremities such as fingers and toes. In addition, tissue (e.g., corneas) that cannot be perfused but requires precise hypothermic storage can also be maintained within the claimed device.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. A method of perfusing and oxygenating living tissue, comprising:

providing a living tissue preservation unit, said unit comprising a perfusion compartment and a tissue compartment each capable of containing a perfusate, and a pumping compartment having a gas opening, said perfusion compartment coupled to said tissue compartment by first and second one-way passage means and said tissue compartment comprising at least one flexible wall;

adding a perfusate to said perfusion compartment and said tissue compartment;

immersing living tissue into said perfusate in said tissue compartment;

sealingly interposing a flexible, gas-permeable membrane between said pumping compartment and said perfusion compartment;

supplying gas to said living tissue preservation unit through said gas opening in said pumping compartment to permeate through said membrane between said pumping compartment and said perfusion compartment;

flexing said membrane in a first direction in response to pressure differentials across the membrane so as to displace a perfusate from said perfusion compartment through said first passage means into said tissue compartment;

flexing said membrane in second direction opposite to said first direction to displace perfusate from the tissue compartment through said second passage means into said perfusion compartment; and removing gas from said living tissue preservation unit by allowing permeation of said gas through said membrane from said perfusion compartment to said pumping compartment and exhausting said gas from said pumping compartment.

2. The method as recited in claim 1, said method further comprising chilling said living tissue preservation unit.

3. The method as recited in claim 1, the method further comprising connecting an inlet vessel of said living tissue to said first one-way passsage means.

* * * * *